United States Patent
French

(10) Patent No.: US 6,180,069 B1
(45) Date of Patent: Jan. 30, 2001

(54) CLEANING SYSTEM AND METHOD FOR CLEANING A FLOW RESTRICTOR IN A SUPERCRITICAL FLUID EXTRACTION SYSTEM

(75) Inventor: James L. French, Holland, MI (US)

(73) Assignee: Leco Corporation, St. Joseph, MI (US)

( * ) Notice: Under 35 U.S.C. 154(b), the term of this patent shall be extended for 0 days.

(21) Appl. No.: 09/252,327

(22) Filed: Feb. 18, 1999

(51) Int. Cl.$^7$ .................................................. B01D 11/04
(52) U.S. Cl. .............................. 422/256; 422/70; 134/40; 210/198.2
(58) Field of Search .................................. 422/256, 285, 422/78, 69, 70; 210/198.1, 198.2; 134/40

(56) References Cited

U.S. PATENT DOCUMENTS

| | | |
|---|---|---|
| 5,147,551 | 9/1992 | Averette . |
| 5,173,188 | 12/1992 | Winter et al. . |
| 5,193,703 | 3/1993 | Staats, III et al. . |
| 5,296,145 | 3/1994 | Allington et al. . |
| 5,578,201 | 11/1996 | Collier et al. . |
| 5,637,209 | 6/1997 | Wright et al. . |
| 5,647,976 | 7/1997 | Rothe et al. . |
| 5,660,727 | 8/1997 | Gleave et al. . |
| 5,670,048 | 9/1997 | Davison et al. . |
| 5,792,357 * | 8/1998 | Wai et al. ............................. 210/638 |

OTHER PUBLICATIONS

H. Engelhardt et al, J. Chromatogr. Sci. 1993, 31, 13–19, Jan. 1993.*
SFX Supercritical Fluid Extraction from Isco, Feb., 1996.
Super Critical Fluid Extraction as a Method for Fat Determination, A Marketing Report, 1987.
Supercritical Fluid Extraction, by Dionex, Jan., 1993.
Supercritical Fluid Extraction and Its Use in Chromatogrphic Sample Preparations, Blackie Academic (published more than one year ago).
Supercritical Fluid Technologies Inc. brochure (1996).

* cited by examiner

Primary Examiner—Arlen Soderquist
(74) Attorney, Agent, or Firm—Price, Heneveld, Cooper, DeWitt & Litton

(57) ABSTRACT

A source of oxidizing gas is coupled to a flow restrictor during a cleaning cycle in which the flow restrictor is heated to a temperature for a period of time sufficient to oxidize and remove built up residue from prior analysis. In one embodiment compressed air is supplied at a pressure of from 20 to 40 psi into the flow path for supercritical fluid, while at the same time the flow restrictor is heated to a temperature of from 300° to 400° C. to oxidize and remove built up residue. A heater assembly employs a resistance heater positioned to heat the restrictor for a period of approximately 12 hours, such that the system can be cleaned overnight when analyses are not normally performed.

18 Claims, 4 Drawing Sheets

CLEANING SYSTEM AND METHOD FOR CLEANING A FLOW RESTRICTOR IN A SUPERCRITICAL FLUID EXTRACTION SYSTEM

BACKGROUND OF THE INVENTION

The present invention relates to supercritical fluid extraction apparatus and particularly to a system for cleaning flow restrictors employed in such apparatus.

The use of supercritical fluid extraction is known for the analysis of the content of fat in samples. One such system that is commercially available is the FA-100 fat analyzer manufactured by Leco Corporation of St. Joseph, Mich. In this system, a carrier fluid such as liquefied carbon dioxide is heated under pressure from 31° to 150° C. to become a supercritical fluid that passes through a heated extraction assembly in which samples are placed. The supercritical fluid and solvated sample then flows through a flow restrictor, preferably a heated variable restrictor valve, and subsequently into a trap for the collection of fat contained in the sample. Although in the preferred embodiment heated variable restrictor valves are employed, other flow restrictors for the purposes of removing the fat content of a sample, such as capillary tubes or manually adjusted restrictor valves, can also be employed.

With such systems, the flow restrictor eventually becomes clogged with the sample material extracted, which is deposited in the restrictor until at some point in time it prevents the proper functioning of the equipment. It is necessary, therefore, to remove and clean the flow restrictors from the system on a schedule which is a function of how often the equipment is being used but can be required on at least a monthly basis. This requires an operator to disconnect and remove the flow restrictors from the system, clean the flow restrictors either mechanically or chemically or both, and subsequently reassemble the apparatus, resulting in significant cost as well as down time for the operation of the system.

SUMMARY OF THE INVENTION

There exists a need, therefore, for a system in which the restrictor in a supercritical fluid fat analyzer can be cleaned without requiring disassembly of the system and one which minimizes interference with the operation of the system and requires little operator intervention. The system of the present invention accomplishes these goals by providing a source of oxidizing gas which flows through the system during a cleaning cycle in which the flow restrictors are heated for a period of time sufficient to oxidize and remove the built up residue from prior analysis. In a preferred embodiment of the invention, the source of oxidizing gas is compressed air which is supplied at a pressure of from about 20 to about 40 psi into the normal flow path for the supercritical fluid, while at the same time the flow restrictors are heated to a temperature of from about 300° to about 400° C. and preferably about 350° C. In a preferred embodiment of the present invention, a heater assembly employs a resistance heater that is positioned to heat a plurality of heated variable restrictor valves employed in a system. In a preferred embodiment of the invention also, the cleaning cycle is automatically timed for a period of approximately 12 hours, such that the system can be cleaned overnight when analyses are not normally performed.

With such a system and method, therefore, the flow restrictors are cleaned without requiring removal of the flow restrictors from the analyzer, their disassembly and mechanical and/or mechanical and chemical cleaning, reassembly, and reattachment. Further, the system of the present invention can be used to clean the flow restrictors automatically during time periods when the system is not in operation and requires only the entry of a clean cycle command by an operator, therefore, eliminating the time consuming operator intervention required in prior art systems.

These and other features, objects and advantages of the present invention will become apparent upon reading the following description thereof together with reference to the accompanying drawings.

DETAILED DESCRIPTION OF THE PREFERRED EMBODIMENT

Figure 1:
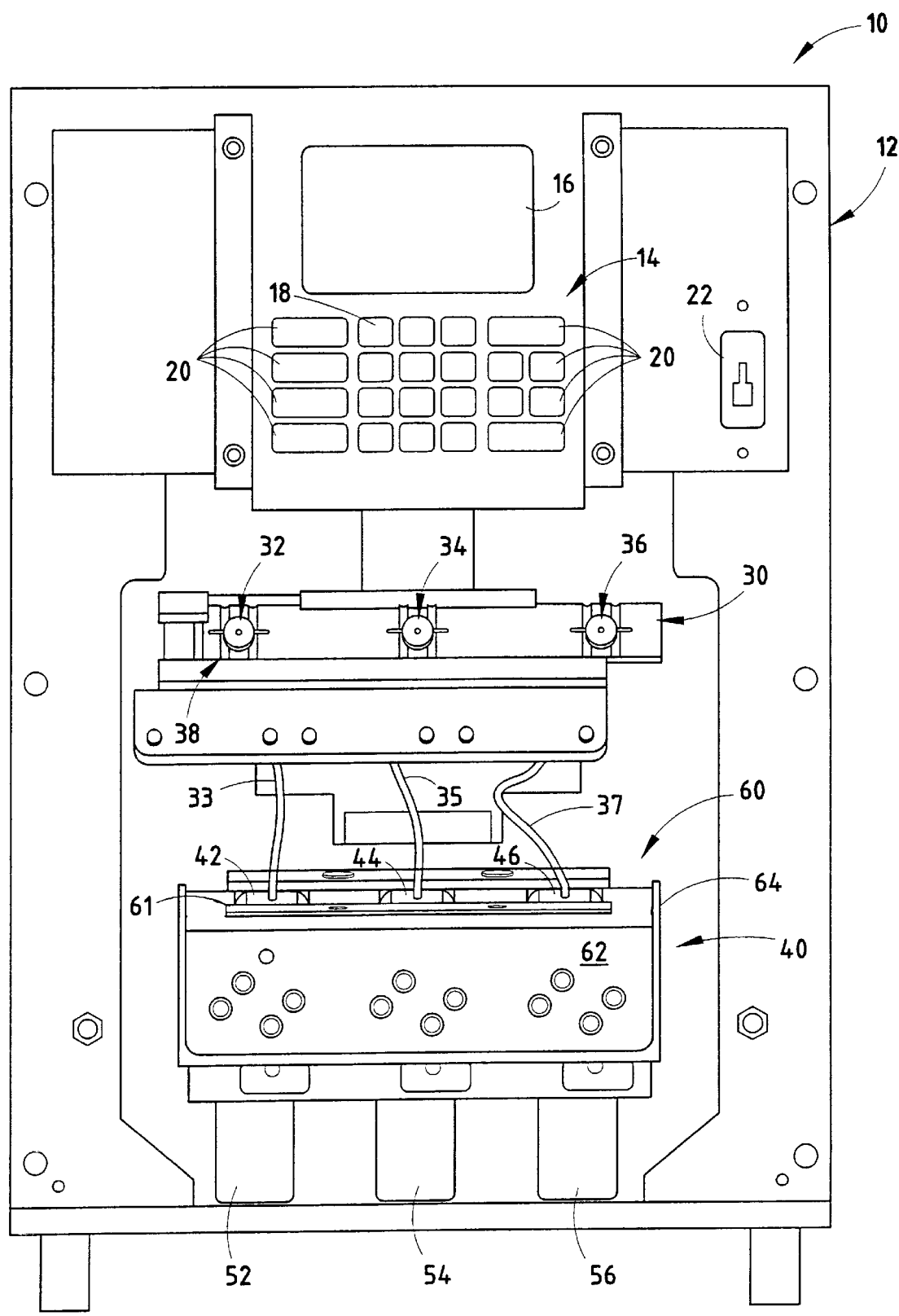
FIG. 1 is a front elevational view of a fat analyzer embodying the system of the present invention.

Referring initially to FIG. 1, there is shown a fat extraction analyzer 10 embodying the present invention. The analyzer is mounted in a cabinet 12 shown in FIG. 1 with the decorative front panels removed. At the upper part of instrument 10, there is provided an electronic module 14 including a display 16, which can be an LCD display or other conventional alpha/numeric type display in common use. The electronic module 14 also includes a numerical entry keyboard 18 and a plurality of control switches 20 to the left and right sides of the numerical entry keyboard. A master on/off switch 22 is also supplied for the instrument in the upper area of the instrument, conveniently located for operator control. The electronic module 14 includes a microprocessor 120 and other circuit elements shown in FIG. 3.

Below the electronic module 14, mounted in cabinet 12 is the extraction assembly 30 which in the preferred embodiment includes three high pressure vessels 32, 34, and 36, which are mounted in a heater assembly 38 for heating the vessels to a temperature of about 100° C. during operation of the instrument. The construction and coupling of the vessels 32, 34, 36 and extraction assembly 30 is described in detail in U.S. patent application Ser. No. 08/801,586, filed on Feb. 28, 1997, entitled HIGH PRESSURE CONTAINMENT ASSEMBLY, now U.S. Pat. No. 5,879,634, the disclosure of which is incorporated herein by reference. This arrangement allows the simultaneous extraction of fat or other analyte from three different samples or, for statistical reasons, from three identical samples.

The extraction assembly, as described in greater detail below in FIG. 2, has inputs coupled to a source of supercritical fluid and has outputs coupled to a restrictor assembly 40 which includes three heated variable restrictor valves 42, 44, and 46, which are needle pin valves controlled to allow the supercritical fluid to flow through the system while carrying extracted fat from the specimen positioned in the vessels of the extraction assembly into matrix traps 52, 54, and 56 coupled to the output of restrictors 42, 44, and 46, respectively, for collecting fat. The matrix comprises glass wool or other suitable material, which is mounted within the glass traps 52, 54, and 56, as seen in FIG. 1. The traps are vented to the atmosphere while collecting the sample material therein. The removable traps are weighed prior to and subsequent to the analysis to determine the weight of fat collected therein. Positioned in thermal proximity with the heated variable restrictor valves 42, 44, and 46 is an aluminum block heater assembly 60 for selectively heating the restrictor assembly 40 during the cleaning cycle of operation, as described in greater detail below. The heater assembly comprises a generally rectangular block 61 of aluminum extending vertically and mounted to the cabinet 12 by a frame 64 in contact with the front of each of the restrictors 42, 44, and 46. Surrounding the sides and front of block 61 is a layer of high temperature insulation 62 to allow heat from the block to efficiently be transferred to the restrictors. A 300 watt resistance heater 66 (FIG. 3) mounted in the aluminum block 61 for heating the restrictors to a temperature from about 300° to about 400° C. and preferably about 350° C. for a predetermined time period up to 16 hours during the cleaning cycle of operation. It is noted that in FIG. 2, the heater assembly 60 is shown below the restrictors only to be able to show the schematic illustration of the commercially available restrictor valves. Having briefly described the overall instrument, a description first of a cycle of analysis is presented, followed by a description of the cleaning cycle with reference to FIGS. 2–4.

Figure 2:
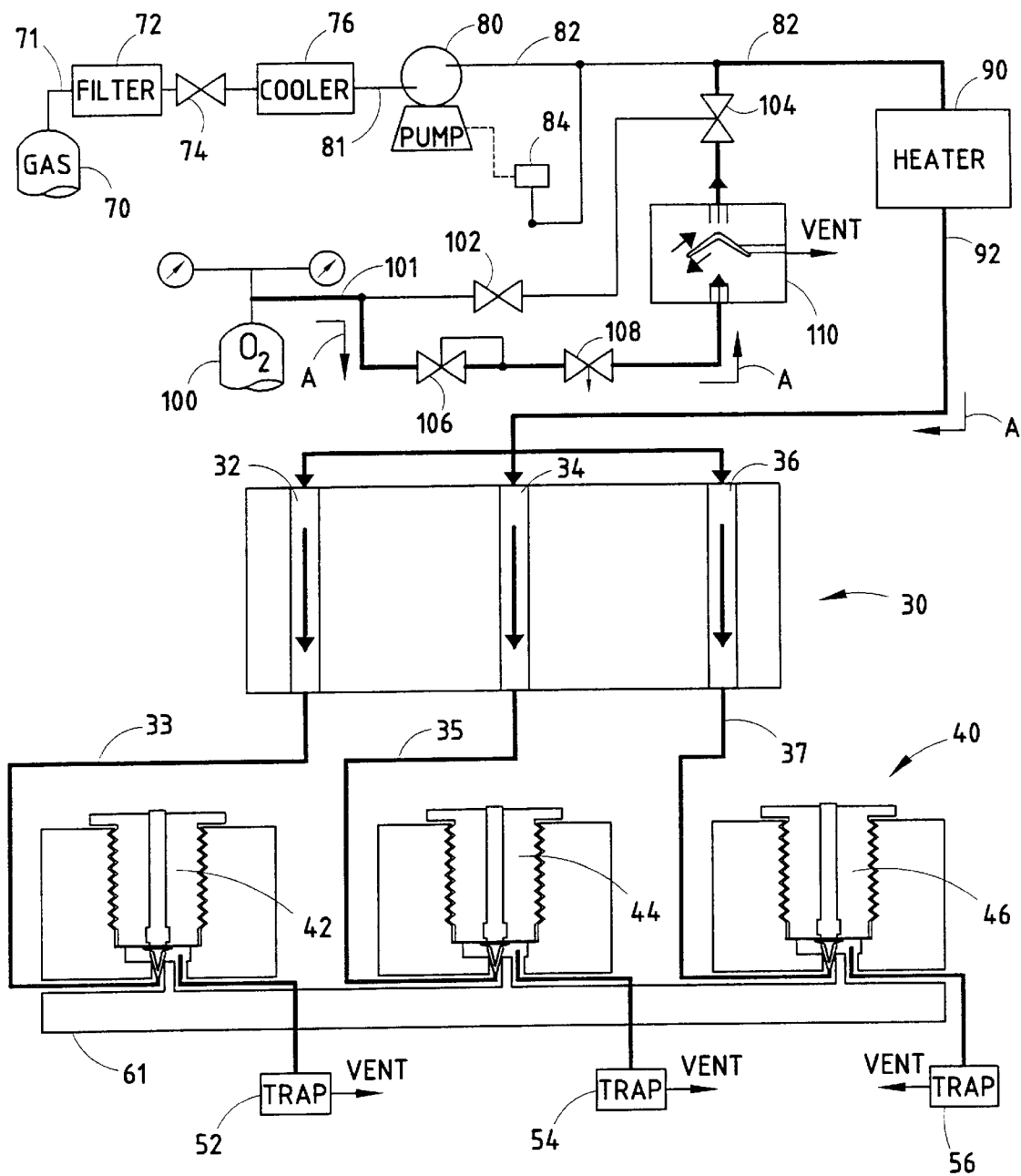
FIG. 2 is a schematic form flow diagram of the structure shown in FIG. 1.

In FIG. 2, a pressurized carrier liquid, such as carbon dioxide, is supplied to the system from a tank 70 and is coupled to a 2 micron filter 72 by a conduit 71. The flow of the pressurized liquid is controlled through an on/off solenoid 74 with the liquid then flowing into a cooler 76 which cools the liquefied $CO_2$ to a temperature below 5° C. The liquid is then supplied to the input 81 of a high pressure pump 80 having an output 82 to which a pressure transducer 84 is coupled. A feedback control circuit (not shown) is employed to maintain the pressure at output conduit 82 of from about 9,000 to about 10,000 psi by controlling the pump operation. The high pressure liquid is then supplied to a heater 90 which heats the liquid carrier to about 100° to about 150° C., such that at output conduit 92, a supercritical fluid having the characteristics of both a gas and a liquid used for extracting fat from a sample placed in vessels 32, 34, and 36 is achieved. Conduit 92 is coupled to the vessels 32, 34, and 36 which are described in detail in the above-identified U.S. Pat. No. 5,879,634, the disclosure of which is incorporated herein by reference.

Samples are placed in vessels 32–36, that are subsequently sealed in the extraction assembly 30. The supercritical fluid flows through the samples and the solvated samples flow through the exit conduits 33, 35, and 37 at a temperature of approximately 100° C. to the input of the heated variable restrictors 42, 44, and 46 of the restrictor assembly 40. The output of the restrictors is then coupled to the traps 52, 54, and 56, respectively, which trap the specimen material in the trapping media, such as a glass wool matrix. The restrictors control the flow rate of the supercritical fluid and allow the pressure to reduce to near atmosphere in the traps, thus revaporizing the liquefied carrier and allowing the specimen fat to be deposited in the matrixes in the collection traps. The now reduced pressure carrier is vented as a $CO_2$ gas to the atmosphere. The high pressure supercritical fluid thus extracts the analyte from the specimen and is metered to allow subsequent collection in the trap by the flow restrictor assembly 40 which, in the preferred embodiment, comprises a variable flow rate needle pin valves but which also can comprise capillary tubes or manually controlled needle valves to throttle the high pressure supercritical fluid to allow the analyte to be deposited at near atmospheric pressure on the trap material. During successive analytical cycles, some of the fatty material is deposited in the restricted flow areas of the restrictors until eventually the flow rate of supercritical fluid is insufficient to effectively remove analyte from the samples in extraction assembly 30. The restrictors, regardless of their design, all suffer from this problem and must be periodically cleaned. In the past, this has required their removal from the instrument 10, disassembly, cleaning, reassembly, and reinstallation. A costly and time consuming process preventing use of the instrument during cleaning. To eliminate this problem, the instrument of the present invention provides a method and structure for the cleaning of the restrictors without requiring their removal or disassembly.

In addition to the flow path described above for providing an analysis of a specimen, a source of oxidizing gas 100 (FIG. 2) comprising, in the preferred embodiment, compressed air is also supplied and coupled in a flow path indicated by arrow A in FIG. 2 through the system for cleaning the restrictors during a cleaning cycle of operation. Prior to cleaning, the oxygen source, having a pressure of approximately 250 pounds, is coupled to a pneumatically actuated high pressure ball valve 104 through a solenoid 102 for initially venting the high pressure liquefied gas from conduit 82 through a shuttle valve 110 to atmosphere, thus reducing the pressure within the system. A pressure regulator 106 is coupled to conduit 101 extending from the source of oxidizing gas 100 to reduce the pressure from the approximate 250 psi to approximately 20 to 40 psi and preferably 30 psi. A three-way solenoid 108 can be actuated to be closed, to vent the system to atmosphere, or to allow the reduced pressure oxidizing gas from supply 100 to flow, as indicated by arrow A, through shuttle valve 110 through ball valve 104 and to conduit 82 through the normal flow path of the system during analysis as described above but for purposes of cleaning the system under the influence of the heater assembly 60 and an oxidizing gas.

Figure 3:
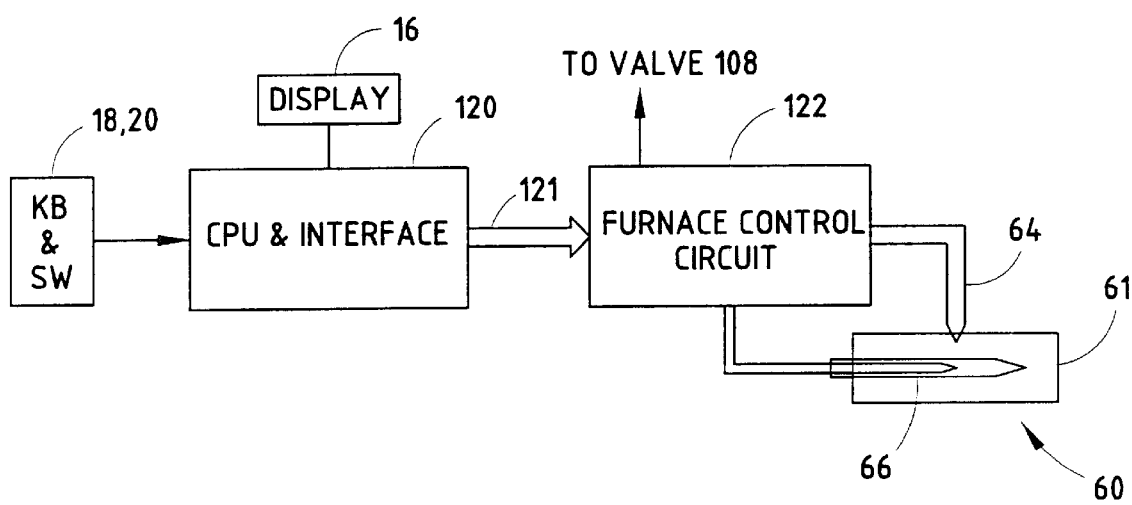
FIG. 3 is a block and schematic electrical circuit diagram of circuit employed to control the cleaning of the system shown in FIGS. 1 and 2.

As seen in FIG. 3, the system includes a central processing unit (CPU) 120 and interface circuits coupling the CPU to the display 16, the keyboard 18, and control switches 20 and to a furnace control circuit 122, which receives input signals from a thermocouple 64' from the heater assembly 60, which includes a resistance heater 66 and the aluminum block 61. The furnace control circuit, once programmed for operation for a predetermined period of time, receives control signals from CPU 120 along bus 121 to activate resistance heater 66 for such predetermined period of time of from about 10 to about 14 hours and preferably about 12 hours. The furnace control receives temperature representative signals from thermocouple 64 and provides a closed-loop control of the heater assembly 60 from about 300° to about 400° C. and preferably about 350° C. for such predetermined period of time, during which time the solenoid valve 108 is also open to allow oxidizing gas from source 100 to flow through the system. With the flow of oxidizing gas and the elevated temperature, the residual material collected in the restrictor assembly 40 is oxidized and slowly burned off and allowed to flow through traps 52, 54, and 56 and be vented to the atmosphere.

Figure 4:
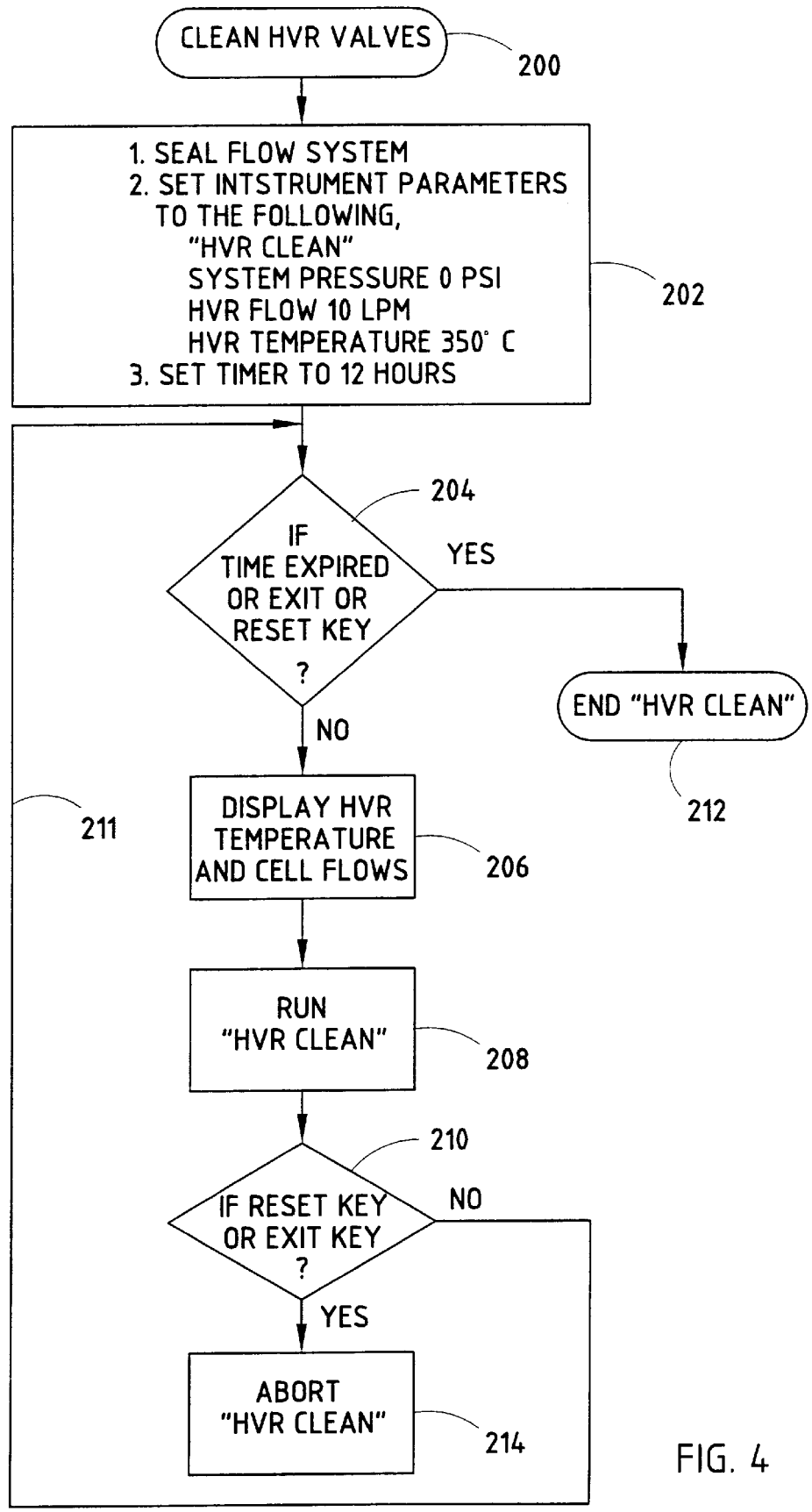
FIG. 4 is a flow diagram of the programming for the microprocessor employed to operate the cleaning system of the present invention.

The control of the microprocessor 120 during the automatic cleaning cycle is shown in the flow diagram of FIG. 4. It is understood by those skilled in the art that the circuit 120 includes a microprocessor and conventional interface circuits coupling the microprocessor to the various electromechanical valves and controls of the system to effect the programmed sequence of operation now described. The program is initiated at block 200 by entry of a command "Clean HVR Valves" by one of the control switches 20 on instrument panel 14. As indicated by block 202, the microprocessor responds to this initial command by controlling the valves to seal the entire flow system, set the instrument parameters to provide a flow rate of 250 cc per minute through shuttle valve 110 and control the heater assembly 60 temperature to about 350° C. and set a timer for, in the preferred embodiment, about 12 hours. The program then proceeds to block 204 to determine whether the time has expired and, if not, displays, as indicated by block 206, the temperature and flow rate of oxidizing gas through the heated variable restrictors (HVR) 42, 44, and 46. The HVR clean cycle continues, as indicated by block 208, unless, as indicated by the test in block 210, a reset or exit key has been actuated by an operator. If not, the program continues through loop 211 to block 204 until the time has expired and the end of the cleaning cycle is reached, as indicated by block 212. If the timer has not expired, the program cycles through the same loop until either the timer has expired or the reset or exit key has been actuated, as indicated by a yes decision in block 210, at which time the cleaning cycle is aborted, as indicated by block 214, also ending the cleaning cycle.

Thus, with the system of the present invention, the restrictors for use in connection with the supercritical fluid extraction system, particularly one for fat analysis, can be cleaned without disassembly and with minimal operator intervention. Such a system greatly increases the use of the analyzer, which can be cleaned as required on either a monthly or quarterly schedule or more frequently if necessary, to maintain the system in good operational condition, with the cleaning being made available during time periods when the instrument is typically not in use.

It will become apparent to those skilled in the art that various modifications to the preferred embodiment of the invention as described herein can be made without departing from the spirit or scope of the invention as defined by the appended claims.

The invention claimed is:

1. An apparatus for the analysis of a sample comprising:
   an extraction assembly;
   a source of supercritical fluid;
   a source of oxidizing gas;
   a conduit including a valve for selectively coupling said source of supercritical fluid and said source of oxidizing gas to said extraction assembly;
   a flow restrictor coupled to said extraction assembly;
   a heater thermally coupled to said flow restrictor; and
   a control circuit coupled to said heater and to said valve to actuate said heater and actuate said valve to heat the flow restrictor and supply oxidizing gas which flows through said flow restrictor for a predetermined period of time to clean said flow restrictor.

2. The apparatus as defined in claim 1 wherein said oxidizing gas includes oxygen.

3. The apparatus as defined in claim 2 wherein said oxidizing gas is compressed air.

4. The apparatus as defined in claim 1 wherein said heater heats said flow restrictor to a temperature of from about 300° C. to about 400° C.

5. The apparatus as defined in claim 4 wherein said heater heats said flow restrictor to a temperature of about 350° C.

6. The apparatus as defined in claim 5 wherein said heater heats said flow restrictor for a period of from about 8 to about 16 hours.

7. The apparatus as defined in claim 6 wherein said heater heats said flow restrictor for a period of time of about 12 hours.

8. A cleaning apparatus for use in an analyzer including an extraction assembly, a source of supercritical fluid, and a flow restrictor for the analysis of fat content in a sample comprising:
   a source of oxidizing gas;
   a conduit for selectively coupling said source of oxidizing gas to said flow restrictor; and
   a controlled heater thermally coupled to said flow restrictor and actuated to heat the flow restrictor while oxidizing gas flows therethrough for a predetermined period of time to clean said flow restrictor.

9. The apparatus as defined in claim 8 wherein said oxidizing gas includes oxygen.

10. The apparatus as defined in claim 9 wherein said oxidizing gas is compressed air.

11. The apparatus as defined in claim 8 wherein said heater heats said flow restrictor to a temperature of from about 300° C. to about 400° C.

12. The apparatus as defined in claim 11 wherein said heater heats said flow restrictor to a temperature of about 350° C.

13. The apparatus as defined in claim 12 wherein said heater heats said flow restrictor for a period of from about 8 to about 16 hours.

14. The apparatus as defined in claim 13 wherein said heater heats said flow restrictor for a period of time of about 12 hours.

15. An apparatus for the analysis of fat content in a sample comprising:
   an extraction assembly;
   a source of supercritical fluid coupled to said extraction assembly;
   a flow restrictor coupled to said extraction assembly and including a controlled heater thermally coupled to said flow restrictor;
   a trap coupled to an output of said restrictor for collecting fat therein;
   a source of oxidizing gas;
   a conduit including an electrically controlled valve for selectively coupling said source of oxidizing gas to said extraction assembly; and
   a control circuit coupled to said controlled heater and to said electrically controlled valve to actuate said heater to heat the flow restrictor and control said electrically controlled valve to provide a flow of oxidizing gas for a predetermined period of time through said flow restrictor to clean said flow restrictor.

16. The apparatus as defined in claim 15 wherein said oxidizing gas is compressed air.

17. The apparatus as defined in claim 16 wherein said heater heats said flow restrictor to a temperature of about 350° C.

18. The apparatus as defined in claim 17 wherein said heater heats said flow restrictor to about 350° C. for a period of time of about 12 hours.

* * * * *